(12) United States Patent
Tanner

(10) Patent No.: US 7,239,910 B2
(45) Date of Patent: *Jul. 3, 2007

(54) METHODS AND DEVICES FOR TRANSCRANIAL MAGNETIC STIMULATION AND CORTICAL CARTOGRAPHY

(75) Inventor: Philipp Tanner, München (DE)

(73) Assignee: BrainLAB AG, Feldkirchen (DE)

( * ) Notice: Subject to any disclaimer, the term of this patent is extended or adjusted under 35 U.S.C. 154(b) by 574 days.

This patent is subject to a terminal disclaimer.

(21) Appl. No.: 10/134,978

(22) Filed: Apr. 29, 2002

(65) Prior Publication Data

US 2003/0023159 A1     Jan. 30, 2003

(30) Foreign Application Priority Data

Jun. 28, 2001 (EP) .................................. 01114823
Feb. 7, 2002 (EP) .................................. 02002033

(51) Int. Cl.
*A61B 5/0484* (2006.01)

(52) U.S. Cl. .................. 600/544; 600/417; 607/45
(58) Field of Classification Search ................ 600/417, 600/544; 606/130; 607/45
See application file for complete search history.

(56) References Cited

U.S. PATENT DOCUMENTS 3,967,616 A    7/1976   Ross (Continued)

FOREIGN PATENT DOCUMENTS

GB    2 271 931     5/1994

(Continued)

OTHER PUBLICATIONS

T. Krings, et al., "Stereotactic Transcranial Magnetic Stimulation: Correlation with Direct Electrical Cortical Stimulation." *Neurosurgery.* vol. 41, No. 6, Dec. 1997. pp. 1319-1326.

(Continued)

*Primary Examiner*—Scott M. Getzow
(74) *Attorney, Agent, or Firm*—Renner, Otto, Boisselle and Sklar, LLP

(57) ABSTRACT

The invention relates to: a method for stimulating and/or inhibiting at least one point or area of a brain using at least one stimulation device, wherein: the spatial structure of the head or brain is recorded; a three-dimensional simulation model of the surface of the brain is generated from the recording of the spatial structure of the brain; and the stimulation device is arranged relative to the head or brain using the three-dimensional simulation model of the surface of the brain, such that the at least one point or area of the brain can be stimulated using the stimulation device; a device for stimulating and/or inhibiting at least one point or area of a brain, comprising a recording device for detecting the spatial structure of the brain, a computational device for generating a simulation model of the surface of the brain and at least one stimulation or induction device, in particular a coil; a method for determining the function of a particular area of the brain, wherein at least one particular area is stimulated using a stimulation device and the stimulus response is measured at least two different positions, and a device for determining the function of a particular area of the brain, comprising at least one stimulation device and at least two stimulus detection devices.

26 Claims, 16 Drawing Sheets

U.S. PATENT DOCUMENTS

Figure 1:
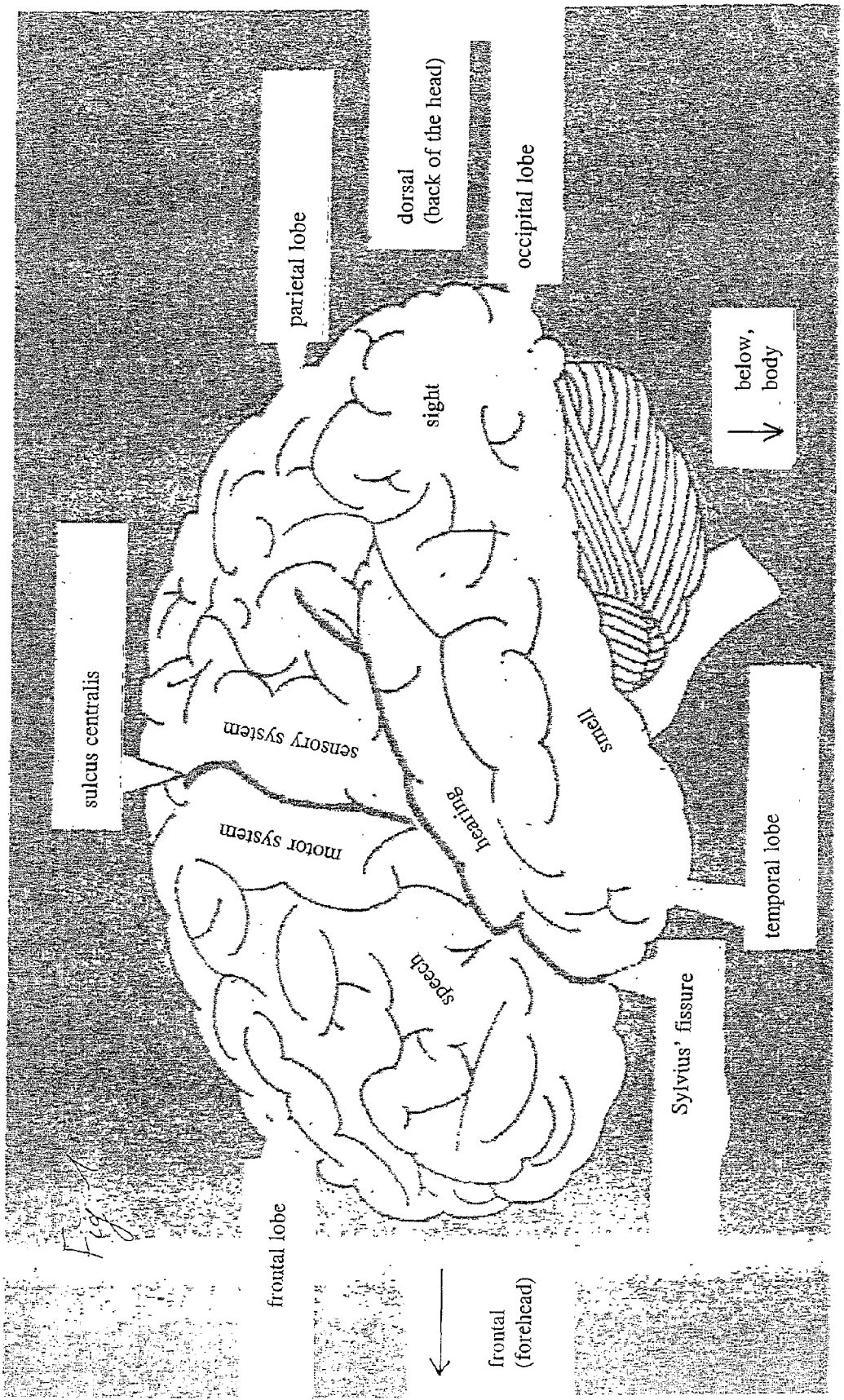

| | | | |
|---|---|---|---|
| 4,805,615 A * | 2/1989 | Carol | 606/130 |
| 4,949,725 A | 8/1990 | Raviv et al. | |
| 4,955,891 A * | 9/1990 | Carol | 606/130 |
| 5,078,140 A * | 1/1992 | Kwoh | 600/417 |
| 5,119,816 A | 6/1992 | Gevins | |
| 5,263,488 A | 11/1993 | Van Veen et al. | |
| 5,366,435 A | 11/1994 | Jacobson | |
| 5,441,495 A | 8/1995 | Liboff et al. | |
| 5,501,704 A | 3/1996 | Chang et al. | |
| 5,526,812 A * | 6/1996 | Dumoulin et al. | 600/407 |
| 5,545,191 A | 8/1996 | Mann et al. | |
| 5,644,234 A | 7/1997 | Rasche et al. | |
| 5,687,724 A | 11/1997 | Jewett et al. | |
| 5,738,625 A | 4/1998 | Gluck | |
| 5,769,778 A | 6/1998 | Abrams et al. | |
| 5,823,960 A * | 10/1998 | Young et al. | 600/145 |
| 5,833,600 A | 11/1998 | Young | |
| 6,014,582 A | 1/2000 | He | |
| 6,066,084 A | 5/2000 | Edrich et al. | |
| 6,129,685 A | 10/2000 | Howard, III | |
| 6,132,361 A | 10/2000 | Epstein et al. | |
| 6,179,771 B1 * | 1/2001 | Mueller | 600/13 |
| 6,212,419 B1 * | 4/2001 | Blume et al. | 600/407 |
| 6,234,953 B1 | 5/2001 | Thomas et al. | |
| 6,267,770 B1 * | 7/2001 | Truwit | 606/130 |
| 6,280,376 B1 | 8/2001 | Holcomb | |
| 6,438,399 B1 | 8/2002 | Kurth | |
| 6,463,328 B1 | 10/2002 | John | |
| 6,491,620 B1 | 12/2002 | Davey | |
| 6,516,246 B2 | 2/2003 | Derakhshan | |
| 6,829,500 B2 * | 12/2004 | Landi et al. | 600/426 |
| 7,008,370 B2 | 3/2006 | Tanner et al. | |
| 2003/0050527 A1 * | 3/2003 | Fox et al. | 600/13 |

FOREIGN PATENT DOCUMENTS

| | | |
|---|---|---|
| WO | 98/06342 | 8/1997 |

OTHER PUBLICATIONS

Ettinger, G.J. et al. "Non-invasive functional brain mapping using registered transcranial magnetic stimulation." *Proceedings of the IEEE Workshop on Mathematical Methods in Biomedical Image Analysis.* San Francisco, CA. Jun. 1996, pp. 32-41.

Herwig, U. et al. "Neuronavigation in der Phsychatrie—fokussierte transkranielle Magnetstimulation dei depressiven Patienten." *Nervenheilkunde.* vol. 18, No. 7 (Jun. 1999).

Ruohonen, J. et al. "Focusing and targeting of magnetic brain stimulation using multiple coils." *Medical and Biological Engineering and Computing.* 36.1 (1998): 297-301.

Ettinger, Gil J. et al. "Experimentation with a Transcranial Magnetic Stimulation System for Functional Brain Mapping." Medical Image Analysis. vol. 2, No. 2; Jun. 1998. pp. 133-142.

* cited by examiner

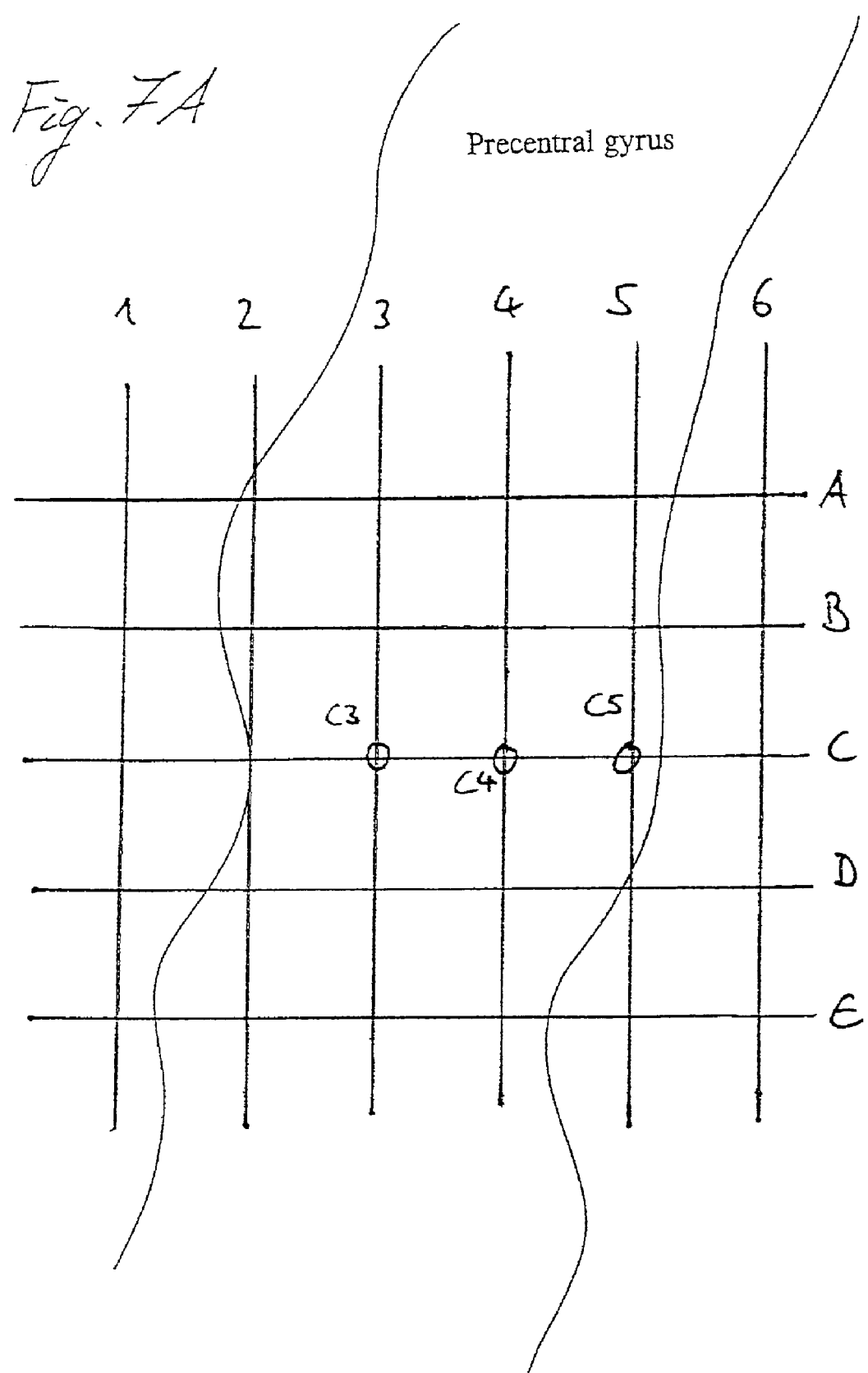

Fig. 7B
C 3
Muscle 1 
Muscle 2 
C 4
Muscle 1 
Muscle 2 
C 5
Muscle 1 
Muscle 2 

eyes visual area          back of the head

METHODS AND DEVICES FOR TRANSCRANIAL MAGNETIC STIMULATION AND CORTICAL CARTOGRAPHY

The present invention relates to methods and devices for transcranial magnetic stimulation (TMS), preferably for navigated TMS, in particular for non-invasively localizing and/or positionally determining particular areas of a brain, such as for example so-called primary or secondary areas of the brain. In this way, for example, brain functions may be mapped, i.e. assigned to certain areas of the brain, which is also referred to as cortical cartography. Equally, it is possible to establish which area of the brain or of a brain convolution (gyrus) fulfils a particular function.

In various areas of medicine, such as for example neurology, psychiatry or brain surgery, it is desirable to be able to localize certain functional areas of the brain, in order to map brain functions. If, for example, a brain tumor is to be removed by surgery, then the tumor should be removed as much as possible, while so-called primary areas of the brain above all, which play a decisive role with respect to a person's motor systems, sensory systems, language or visual capacities, should if possible not be injured. In surgery, these areas should if possible not be injured at all or only to an exceedingly minor extent.

Locating these particular areas of the brain has been performed intra-operatively according to a known direct method, wherein direct cortical stimulation (DCS) was performed on an exposed cranium by means of electrodes. In this way, an electrode was introduced into a particular area of the brain and an electrical impulse applied, the consequent response of the person being examined to the electrical impulse, for example the twitching of a muscle or the perception of visual impressions, being observed. The particular areas of the brain located by direct cortical stimulation were marked by means of small, attached plates which in a subsequent brain operation represents an orientation aid for the surgeon with respect to the areas of the brain which are as far as possible not to be injured. To date, direct cortical stimulation represents the most precise method of mapping brain functions and enables a precision in the range of a few millimeters in locating particular areas of the brain. However, this method can only be performed intra-operatively, the person being examined having to be fully conscious. This, however, can lead to problems when using this method, as this state is unpleasant for the person being examined and, if complications should arise, the person cannot simply be laid down and made to relax, due to their exposed cranium.

Furthermore, various indirect methods for mapping brain functions are known, using which however only a considerably lower precision can be achieved in locating specific areas of the brain. Thus, for example, in functional nuclear spin tomography (fMRI) a person being examined has to perform certain actions, such as for example a sweep of the hand, which promotes blood flow in the areas of the brain assigned to these actions. Due to the decoupling of blood flow and oxygen consumption during neuronal activity, this change in blood flow in particular areas of the brain can be measured, since this causes hyperoxygenation and thus a drop in the concentration of paramagnetic deoxyhaemoglobin (BOLD effect), which can then be measured as a so-called "endogenic contrast medium" by means of suitable sequences, using nuclear spin tomography. However, as mentioned above, this method is relatively imprecise and only provides a spatial resolution in the range of about 0.5 cm to 1.0 cm.

A method is known from Neurosurgery 1992-1998, December 1997, Volume 41, Number 6, 1319 "Stereotactic Transcranial Magnetic Stimulation: Correlation with Direct Electrical Cortical Stimulation", in which stereotactic transcranial magnetic stimulation (TMS) is used for pre-operative functional mapping of the motor cortex. Thus, the head of a patient is securely and immovably connected to a headrest, wherein a rotating arm is provided to which a figure-eight coil is attached such that the tip of the arm is under the intersecting point of the coil. The arm is thus aligned such that the tip under the intersecting point of the two coils points to a particular area in which a current is to be induced.

A method is known from U.S. Pat. No. 5,738,625 for magnetically stimulating nerve cells.

U.S. Pat. No. 5,644,234 described a nuclear spin resonance (MR) method in which the position of a micro-coil in an object is to be determined.

A method and a device for transcranial magnetic stimulation of the brain are known from WO 98/06342, in which a broadly hemispherical magnetic core wound with coils is used to generate a stimulation signal. The described device and method are intended to localize the speech function.

It is an object of the present invention to propose methods and devices for stimulating particular areas of a brain, by which the spatial precision of stimulating and localizing particular areas of the brain can be improved.

This object is solved in the way defined in the independent claims. Advantageous embodiments follow from the subclaims.

Stimulation in the sense of the invention means not only actually, actively stimulating a particular area or point of the brain, but also applying or generating signals which cause certain areas of the brain to be functionally suppressed, also often referred to as functional lesion. The term "stimulate" is accordingly to be understood such that certain stimulation signals can also cause brain functions to be blocked or inhibited. An area of the brain is stimulated or inhibited by applying or generating signals in the brain using a stimulation device such as for example a coil attached to the head and through which current flows, to generate electrical signals in the brain by induction, wherein the signals can be a particular impulse shape or a succession of impulses having particular impulse shapes and one or more predetermined frequencies. It has been shown that certain areas of the brain can be blocked or inhibited using higher frequencies, for example in the range of 50 Hz, such that the functions to be fulfilled by the areas of the brain in question, such as for example perceiving an external stimulus, can no longer be performed. In this respect, stimulation is preferably carried out using a single magnetic or so induced electrical impulse.

In accordance with a first aspect of the invention, in a method for stimulating and/or inhibiting a particular area of a brain, for example an individual point or a cluster or grid of a number of points, using for example an induction device as the stimulation device, the spatial structure of the head or brain to be examined in firstly recorded, for example using nuclear spin resonance (MRI) methods, computer tomography (CT), ultrasound, x-ray, video imaging with subsequent reconstruction of the surface of the brain, or other known examination methods. Based on the spatial structure of the head or brain thus obtained, a simulation model of the surface of the brain is generated. Here, the fact is utilized, in accordance with the invention, that sensory, motor, visual, auditory and olfactory functions are realized by areas on the surface of the brain. Since the brain exhibits an irregular surface, an attempt is made in accordance with the invention to simulate this surface as precisely as possible, in order to perform stimulation based on a stimulation model generated in this way as far as possible orthogonal or normal with respect to the surface of an area to be stimulated. If a stimulation device, such as for example a coil for generating a stimulation signal, such as is common in the prior art, is arranged relative to the surface of the head such that the magnetic field generated by the coil is as normal with respect to the surface of the head as possible, then the irregular surface of the brain could result in an area of the surface of the brain being stimulated by a magnetic field which is not normal with respect to the surface of the brain, and the mutually oblique relative position thus resulting in a larger or even different area of the brain unintentionally being stimulated. In general, an induction device such as for example a coil generates a magnetic field which induces an electrical field for stimulation on and/or in the surface of the brain. Using the method in accordance with the invention, the induction device is accordingly positioned relative to a head or to the surface of a brain, such that the induction device generates a magnetic field which if possible is precisely, or with only a relatively minor deviation of for example 5 degrees, normal with respect to the surface of the brain. It can transpire here that the induction device does not have to be positioned orthogonal to the surface of the head. This is the case in particular when the area on the surface of the brain to be stimulated is not parallel to the surface of the head. In accordance with the invention, a particular area of the brain or of the surface of the brain is to be stimulated by an induction device, preferably by a current flowing in the induction device, such that a stimulation signal is generated on the surface of the brain by a magnetic field which is as normal with respect to the surface of the brain as possible.

Advantageously, the surface of the brain is modelled or approximated using polygons, i.e. based on the data obtained by recording the spatial structure of the brain, polygons are generated which as a plurality of small planes form a three-dimensional model of the surface of the brain and thus represent as it were the walls or outer limit of the surface of the brain. Advantageously, an induction device is then positioned in accordance with the invention, such that if a particular area of the surface of the brain is to be stimulated, the magnetic field generated by the stimulation device is as normal as possible on the polygon or simulated surface of the brain which is to be stimulated. In this way, for example, the stimulation or induction device can be positioned such that it generates a maximum magnetic field approximately in the center of a polygon used to simulate the surface of the brain.

Preferably, one or more elements are used as the stimulation device, which can generate an electrical or magnetic field, such as for example coils with or without a core.

Advantageously, so-called "tracking" of the stimulation device used is performed, wherein the corresponding elements are registered using known methods and devices, such as for example reflecting markers attached to the head and to the stimulation device, and a stimulation device is navigated, i.e. guided and positioned relative to the surface of the brain, such that a magnetic field generated by the stimulation device is as normal as possible on the surface of the three-dimensional stimulation model of the brain and assumes a maximum value at the desired point of stimulation. Methods and devices for positioning and navigating instruments relative to a person are known in the prior art and will not be described in more detail here. By way of example, reference is made to the method described in the Applicant's priority application EP 01 114 823.6, wherein the teaching of this patent application is introduced into the disclosure of this application, in this respect and in particular with respect to generating simulation models of an induction device and/or a head.

Preferably, the position of a stimulation device relative to a desired point to be stimulated is determined and advantageously displayed such that a person can use the position of the stimulation device relative to the desired point of stimulation to place the stimulation device in the desired position for stimulating the point of stimulation. Here, a blockage of the stimulation device, such as for example a blockage of the coil current, can advantageously be provided if for example the angle of a magnetic field which may be generated by the stimulation device deviates by more than a predetermined angle of for example 5 degrees from the normal on the simulated surface of the brain, for example from the normal on a particular polygon over an area to be stimulated. In this way, for example, a magnetic and/or electrical field which may be generated by the stimulation device can be simulated and displayed, to thus test the accuracy of the position of the stimulation device, before actually performing stimulation.

The three-dimensional data set for generating a simulation model of the surface of the brain can vary in its degree of detail over the surface of the brain as a whole, to thus model for example greater, more uniform areas of the brain using a smaller number of polygons, and to model areas of the brain with a greater degree of detail using a greater number of polygons.

The method described above can be used both without and in combination with the method in patent application EP 01 114 823.6 mentioned above, i.e. for example, a simulation model of the head and/or the induction device can also be generated and used to suitably position a stimulation device. In this way, a stimulation device such as for example an induction device can be simply positioned such that a line going through the center of the coil should be normal or at a particular angle on the simulation model, in order to stimulate a desired point. In addition, however, more precise simulation models of the induction device and/or simulation models of the head can be used, using for example a multi-shell model of the head such as is described in EP 01 114 823.6.

It is also possible to use the method described above and the method described in EP 01 114 823.6 together, i.e. for example, the surface of the brain is modelled using the method described above, wherein the electrical and magnetic properties of the structures above the surface of the brain are taken into account in accordance with the teaching of EP 01 114 823.6, in order to be able to position the coil accurately, before stimulation is actually performed.

In accordance with another aspect, the invention relates to a computer program which performs the method comprising one or more of the steps described above when it is loaded on a computer or is running on a computer. Furthermore, the present invention relates to a program storage medium or a computer program product comprising such a program.

According to a further aspect, the invention relates to a device for stimulating a particular area of a brain, comprising a stimulation or induction device, wherein a recording device such as for example a nuclear spin tomograph is provided, in order to record the spatial structure of the head, in particular of the brain. Based on the data thus obtained, a simulation model is generated in a computational device, to three-dimensionally approximate or simulate the surface of the brain.

A navigation device is advantageously provided, which serves to position the stimulation or induction device—which is preferably provided with markers—relative to the head or surface of the brain, such that a particular area of the brain or surface of the brain can be stimulated using an impulse of the stimulation device, for example a current flowing in an induction device.

Preferably, a control device is provided, advantageously in combination with a display unit, with which the steps of the method described above can be controlled and the positions of for example the stimulation device relative to the head or to the simulated surface of the brain and the stimulation signals can be displayed.

Using the method described above and the device described above enables a stimulation device, such as for example a coil, to be positioned in such a way that a magnetic field generated by the stimulation device meets the surface of the brain to be stimulated as normally as possible, wherein for example the center axis of a coil can in approximation be positioned such that it is normal on a three-dimensional simulation model of the surface of the brain, before one or more impulses are generated.

The method and device described above can also be used to stimulate a single point in the brain and/or on the surface of the brain, also often referred to as a "hot spot". However, in order to locate functional areas in the brain which are responsible for the more complex functions, it is often insufficient to perform transcranial magnetic stimulation on a single point and to use the evoked potentials to determine the position of for example the motor cortex. For it is known that certain brain functions are not realized by narrowly delimited areas of the brain, but can extended or be distributed over large areas. In general, a gyrus—i.e. a brain convolution—often represents the only known "sharp" border of a brain function, wherein the intermediate space between two brain convolutions is referred to as a sulcus. However, different motor functions can for example be realized by different positions on a gyrus, or speech functions for example can be realized by various gyri.

In accordance with a further aspect of the invention, a method is proposed in which at least one particular point of the brain or the surface of the brain is stimulated, wherein at least two, preferably a plurality, for example 8, 32, 100 or more stimulus responses are detected on a person, for example by providing a number of stimulus detection devices at various positions, such as for example on the individual fingers of one hand and/or other muscle groups, so as to obtain information, via multi-channel recording and advantageously multi-channel stimulating, about how a particular stimulation or stimulation pattern applied simultaneously or successively to one or more areas of the brain affects the muscle groups. In this way, it is possible to measure which muscle and/or part of a muscle is moving when and how strongly, when a particular stimulation pattern is applied. Information about how a particular function, such as for example generating a muscle twitch, is actually assigned to a position or an area on a gyrus is obtained from the assignment of stimulation patterns to the stimulus responses recorded via a number of channels. Thus, for example, the functional area can be determined from the measured stimulus responses using a sequential stimulation pattern, after a particular number of stimulation impulses. This method enables functional areas to be localized faster.

A grid structure is advantageously defined, for determining different points of stimulation on the surface of the brain, wherein stimulation impulses can be applied to the intersection points of the grid lines, for example individually and in sequence at different intersection points, or simultaneously at a number of intersection points with the same or with different intensities and the same or different frequency patterns. Preferably, the grid structure is positioned such that the grid is only on one or more functional areas, wherein positioning can be automatic or semi-automatic, i.e. for example, grid points positioned by a computer referring to the three-dimensional model of the brain can be manually adjusted. A stimulation device, such as for example a coil, can be positioned in a known way, as described in EP 01 114 823.6, or using the methods and devices described above.

If, for example, an area of the motor cortex is stimulated, then it is relatively simple to measure the strength of the stimulus response, in this case a muscle twitch. In general, the strengths of stimulus responses can also be determined when other brain functions are stimulated, for example the brightness of a perceived flash or the volume of a heard sound.

In this way, for example, a TMS coil can be moved or navigated under computer guidance from one grid point to another, and a stimulation impulse having a predetermined value above a predetermined stimulus threshold can be induced via the TMS coil. All the stimulus responses of a particular stimulation are always recorded simultaneously, and the stimulus response for stimulating an individual grid point or a number of grid points can be determined simultaneously.

Advantageously, a particular stimulation impulse or a stimulation pattern is applied a number of times at the same intensity, in order for example to enable a mean value to be formed or the detected readings to be evaluated differently.

For each stimulus response, i.e. for example for the movement of a particular muscle, a distribution function or intensity function of the representation of the motor guidance of said muscle on the motor cortex can advantageously be determined, using the method described above. In other words, by simultaneously recording a number of stimulus responses with particular stimulation patterns, a particular stimulus response, such as for example a muscle twitch, can be assigned to a particular area of the brain, wherein areas of the brain having a stronger or weaker correlation to said stimulus response can be determined using the position of the grid points used for stimulation. The intensity or sensitivity function obtained from the individual stimulus responses can be interpreted for example as a three-dimensional distribution over the surface of the brain, wherein the sensitivity function of a first muscle can overlap with the sensitivity function of a second muscle and for example assumes a maximum value at another position.

It is also possible to use a stimulation device in which a number of stimulation impulses can be outputted simultaneously, a plurality of coils for example being arranged in a grid structure such that a number of coils can be applied simultaneously with the same or different stimulation impulses, to generate a number of stimulation impulses on the surface of the brain, wherein it can be determined from the simultaneously measured stimulus responses, which stimulated areas were responsible for triggering a particular stimulus response and with which weighting or transfer function.

In accordance with another aspect, the invention relates to a computer program which performs the method comprising one or more of the steps described above when it is loaded on a computer or is running on a computer. Furthermore, the present invention relates to a program storage medium or a computer program product comprising such a program.

Furthermore, the invention relates to a device for stimulating at least one point of the brain, and at least two recording devices with which the stimulus responses of an impulse induced via the stimulation device can be measured.

In accordance with a first embodiment, the stimulation device is a computer-guided stimulation device which can be positioned as precisely as possible at various positions of the head, or in general relative to the surface of the brain, to generate a stimulation impulse.

In accordance with another embodiment of the invention, the stimulation device is composed of a plurality of individual stimulation devices, such as for example a number of coils, in order to be able to simultaneously induce stimulation impulses at various points of the brain. This stimulation device can likewise be positioned using computer guidance, and furthermore can for example be designed such that the individual induction devices or coils are for example on a spherical or ellipsoid surface, such that they can be attached to a head, wherein the individual stimulation devices should then advantageously exhibit approximately the same distance from the surface of the brain. Alternatively, the distance of individual stimulation devices can be varied, in order to vary the parameters of a stimulation impulse.

A control device is advantageously provided, preferably in combination with a display device, in order to perform at least one of the steps of the method described above and to display various information such as for example the positioning of an induction device relative to the brain, the simulated surface of the brain, a simulation model of the induced impulse, and the like.

The stimulation impulses applied to one or more points of the surface of the brain can be interpreted as an input vector whose individual elements consist of the stimulation impulses. The stimulus responses measured at a number of points can be interpreted as an output vector of a system represented by the brain and can be described in the form of a matrix, in order to obtain the output vector from the input vector mentioned.

In accordance with another aspect of the present invention, the TMS technology described above is used to localize different areas of the brain, such as for example the speech cortex, the visual cortex, the sensory cortex, the auditory cortex or the olfactory cortex, wherein an automatic or automated system is preferably used, to generate a map of the corresponding brain functions.

The problem exists in general that the more complex brain functions are not localized in narrowly delimited areas of the brain, but are realized by the interplay of a number of areas (clusters) of the brain. Impulses can be used for stimulating or inhibiting, for example to obtain a stimulus response to a stimulation impulse or a functional lesion, i.e. short-term function suppression, in order to be able to map, i.e. functionally assign areas of the brain to particular functions, based on said information. Stimulation impulses generally result in particular actions being triggered, such as for example a muscle twitch, or sensory impressions being generated, such as for example optically perceiving a flash, hearing a particular sound, smelling a particular smell or for example perceiving a tactile sensation, such as for example a prick. If an inhibiting signal for generating functional lesions is generated, for example by applying high-frequency impulses, then it can determined which brain function is being blocked, via functional failures of the corresponding area of the brain, established using a test person.

In this way, for example, a particular area of the field of vision can be blocked, a frequency range no longer heard, certain speech functions suppressed, sensory impressions—such as for example a prick—or certain smells no longer perceived.

Particular stimuli, such as for example optical, acoustic, sensory or olfactory impressions, can be presented to a person in a conventional way, to give the person the opportunity to compare these stimuli with stimuli generated by the stimulation methods and stimulation devices described above. In this way, an iterative method can be performed, until the natural sensory impression and the sensory impression generated by TMS correspond as precisely as possible.

With respect to applying or generating stimulation signals, reference is made to the previously described methods and devices.

For locating and examining the visual cortex, a device such as for example a projector or a specialized pair of glasses can be provided, in which the known perimeter of the field of vision, also known as the Goldman perimeter, is represented for example by lines. When a TMS stimulation signal is generated in the area of the visual cortex, a person will perceive an optical impression, such as for example a brief flash, or—according to the type of signal—will no longer identify a particular area of a displayed image. The area of perception of the flash generated by the TMS signal or the loss of an image area in the perimeter of the field of vision can be correlated with the area of the visual cortex at which the stimulation impulse was generated, enabling particular areas of the field of vision to be assigned to particular areas of the visual cortex.

For examining the auditory cortex, a device for generating sounds can be provided, such as for example a loudspeaker or headphones, in order to transfer sounds via the air directly to the person's ear (air conduction). As an alternative, it is also possible to use an electromagnetic vibrator which is placed on a bone in the vicinity of the ear, in order to generate an acoustic impression (bone conduction). In this way, a sound is generated at a constant frequency and in accordance with the TMS stimulation impulses can be either suppressed or used as a reference for a tonal impression induced using TMS. If a TMS stimulation device is moved over different areas of the auditory cortex, a map of the auditory cortex representing the perception of various frequency ranges can be obtained.

The arrangements described above for the visual and auditory cortex can also be used for examining the speech cortex. In this way, for example, a person can be presented with particular optical and aural signals via a monitor and/or headphones. A microphone is preferably provided, to record speech spoken by the person. Various speech paradigms are used, such as for example a naming exercise in which a person has to name an object shown, a reading exercise, an association exercise or an interpretation exercise. The responses given by the person are collected and processed by the computer, to obtain information with respect to the assignment of different speech functions on the speech cortex. For example, it is possible for a computer system to automatically position one or more TMS stimulation devices at various points, using the methods and devices described above, based on the responses given by the person, in order to then be able to examine the speech cortex in as automated a manner as possible.

When examining the speech cortex, it must be considered that—unlike, for example, with the motor cortex—it is not generally possible to assign stimulation impulses to the stimulus response, since the various functions necessary for speech sensation and/or speech performance are distributed over a number of areas of the brain.

For examining the sensory cortex, a person can be presented for example with a depiction of the human body, wherein a person is supposed to point to areas of the depiction in which he/she has a sensory impression caused by TMS stimulation. Alternatively, a person can also point to the respective part of their own body or can communicate by speech where a sensory impression has just been generated. Equally, a sensory impression can be blocked by inhibiting, i.e. a test person no longer feels a sensory stimulus, such as for example a prick, when for example appropriate TMS signals are applied.

For examining the olfactory cortex, a person can be offered a test series of odors. A TMS stimulus is then applied to particular areas of the olfactory cortex. A person can compare the smell perceived via the nose with the smell generated in the brain by the TMS stimulation signal, and for example by repeating the method a number of times, iteratively determine which actually perceived smell best corresponds to the smell generated by TMS, thus mapping the olfactory cortex.

In accordance with another aspect, the invention relates to a computer program product which performs the method comprising one or more of the steps described above when it is loaded on a computer or is running on a computer. Furthermore, the present invention relates to a program storage medium or a computer program product comprising such a program.

A device in accordance with the invention, for determining a particular area of the brain, comprises at least one device for stimulating and/or inhibiting at least one particular area of the brain, and a device for generating a visual and/or acoustic and/or sensory and/or olfactory sensory impression. In particular, the device is to be designed such that it is suitable for performing the steps of the method described above.

Using the methods and devices described above, it is intended in accordance with the invention that individual areas of the brain are automatically and precisely stimulated, preferably using known navigation methods comprising for example passive markers, the stimulus response is automatically detected, and if necessary stimulation patterns are automatically modified for a subsequent stimulation. In this way, the function of a particular area of the brain can for example be simply determined by automatically and preferably with navigation positioning a stimulation device on a person to be examined in order to generate automatically generated stimulation patterns at one or more points sequentially and/or simultaneously at particular areas of the brain, wherein the stimulus response or responses is/are measured, either automatically—for example using sensors attached to muscles—or by interaction with the person to be examined, who is asked about particular sensory impressions or who gives statements of their own accord about these, possibly by comparison with a reference stimulus or by observing the test person solving preferably automatically set exercises, as for example when examining the speech cortex.

Although the invention has been described by way of a number of aspects, the individual aspects of the invention can also be used in combination with each other, i.e. three-dimensional simulation models of the surface of the brain can for example be used when stimulating one or more areas of the brain and when automatically detecting one or more stimulus responses, wherein for example the functional distribution of the speech cortex is automatically determined by particular exercises being set via a computer screen, which address different speech functions of various areas of the brain, and automatically detecting the solutions to the exercises set for example by speaking into a microphone or inputting into a keyboard. Then, one or more stimulation devices can for example be re-positioned and/or an applied stimulation impulse for stimulating and/or inhibiting can be changed, according to the results thus obtained, whereupon the same or a different test is performed so as to be able to automatically localize functional areas of the brain. In general, the invention can also be used for semi-automatically localizing particular areas of the brain, wherein for example a supervisor intervenes in the test sequence and can change particular test sequences.

Figure 2:
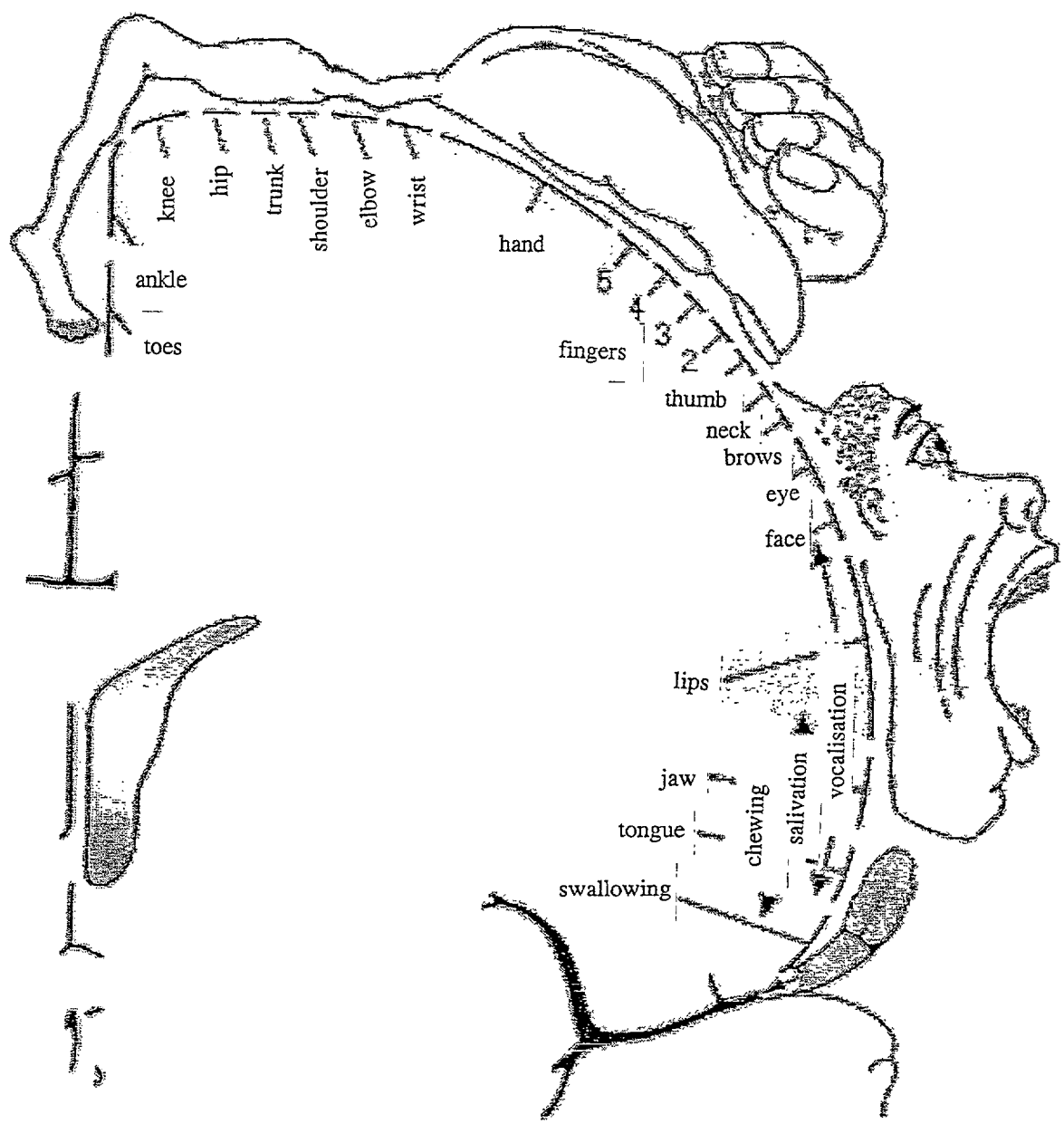
Figure 3A:
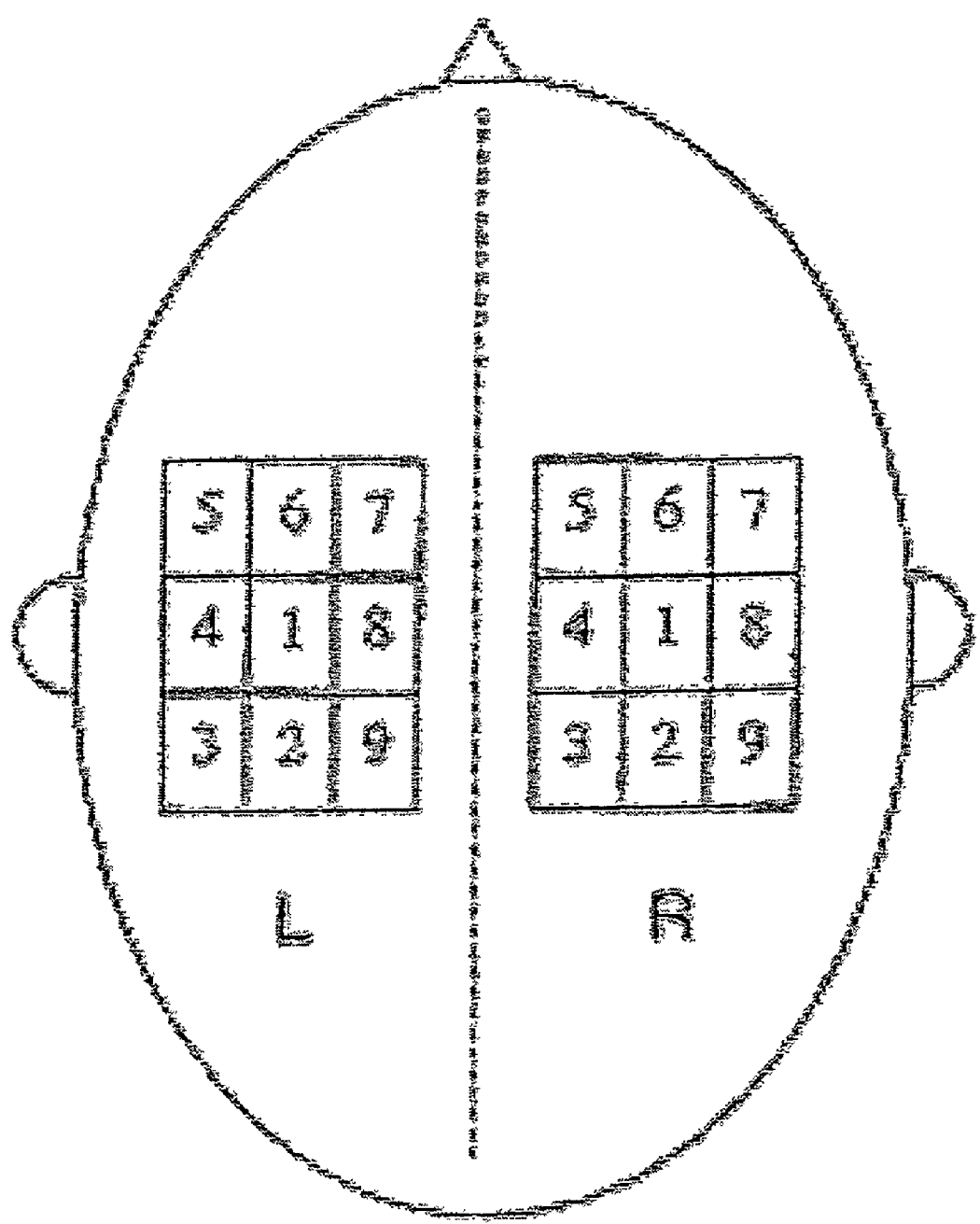
Figure 3B:
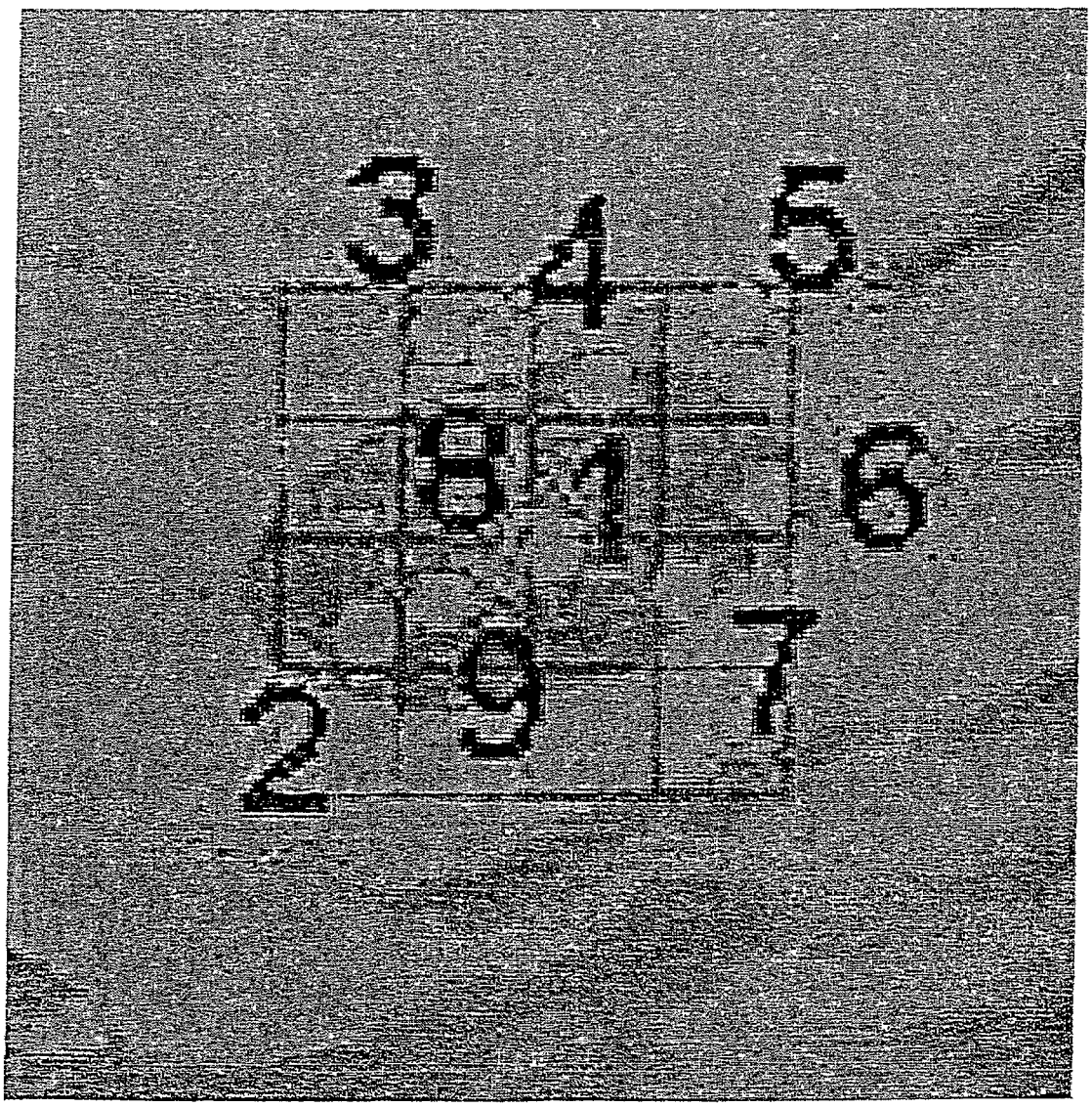
Figure 4A:
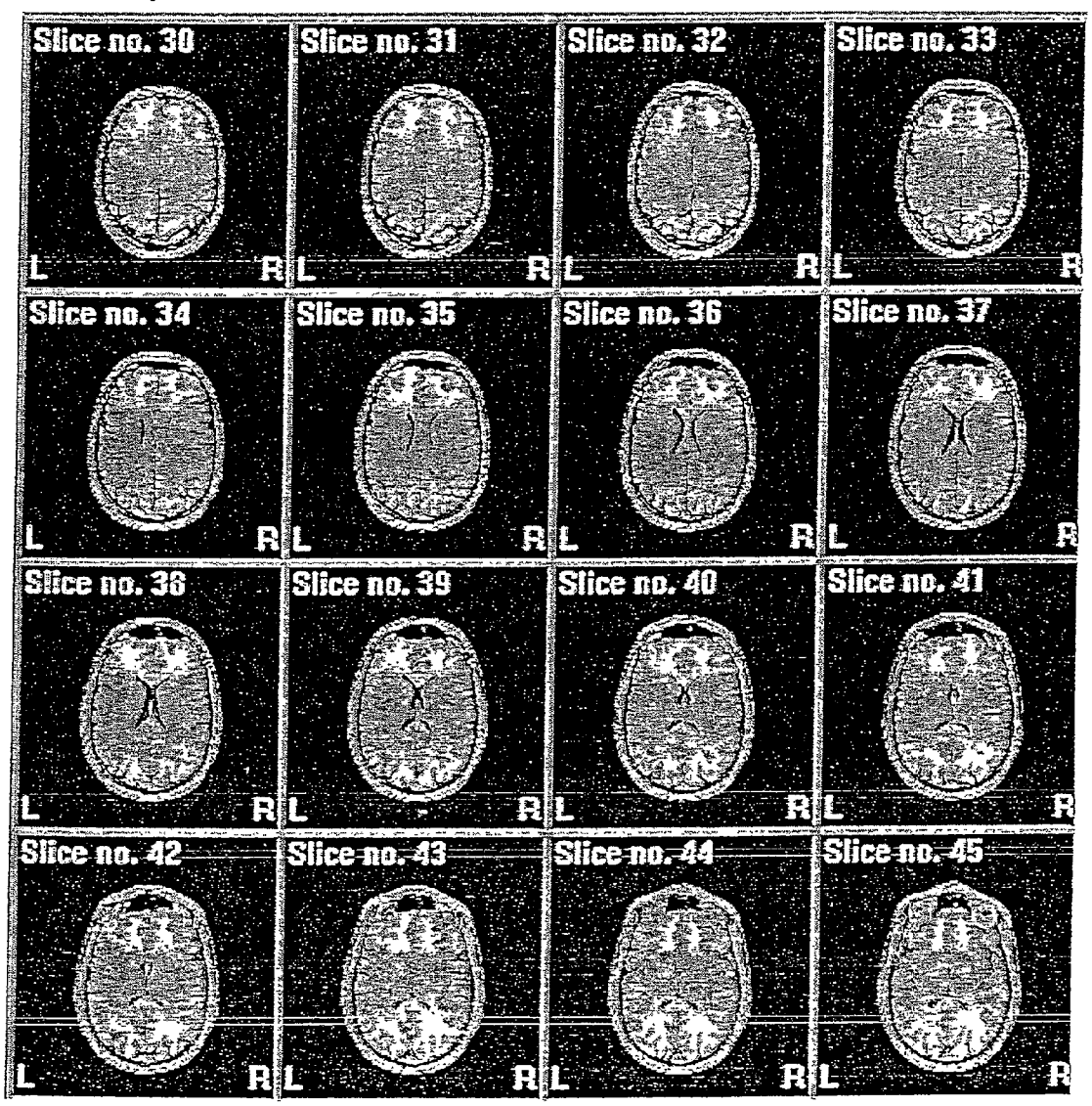

The invention will now be described by way of example embodiments, and referring to the enclosed drawings. There is shown:

FIG. 1 the schematic distribution of brain functions over the brain;

FIG. 2 shown schematically, the distribution of motor functions over the gyrus;

FIG. 3A a test pattern for predetermining stimulation locations, in accordance with the prior art; and FIG. 3B the deviation between the locations of the actual stimulation impulses and the predetermined stimulation locations, due to positioning inaccuracies;

FIG. 4A MRI tomographs of a brain recording; and

Figure 4B:
Figure 5:
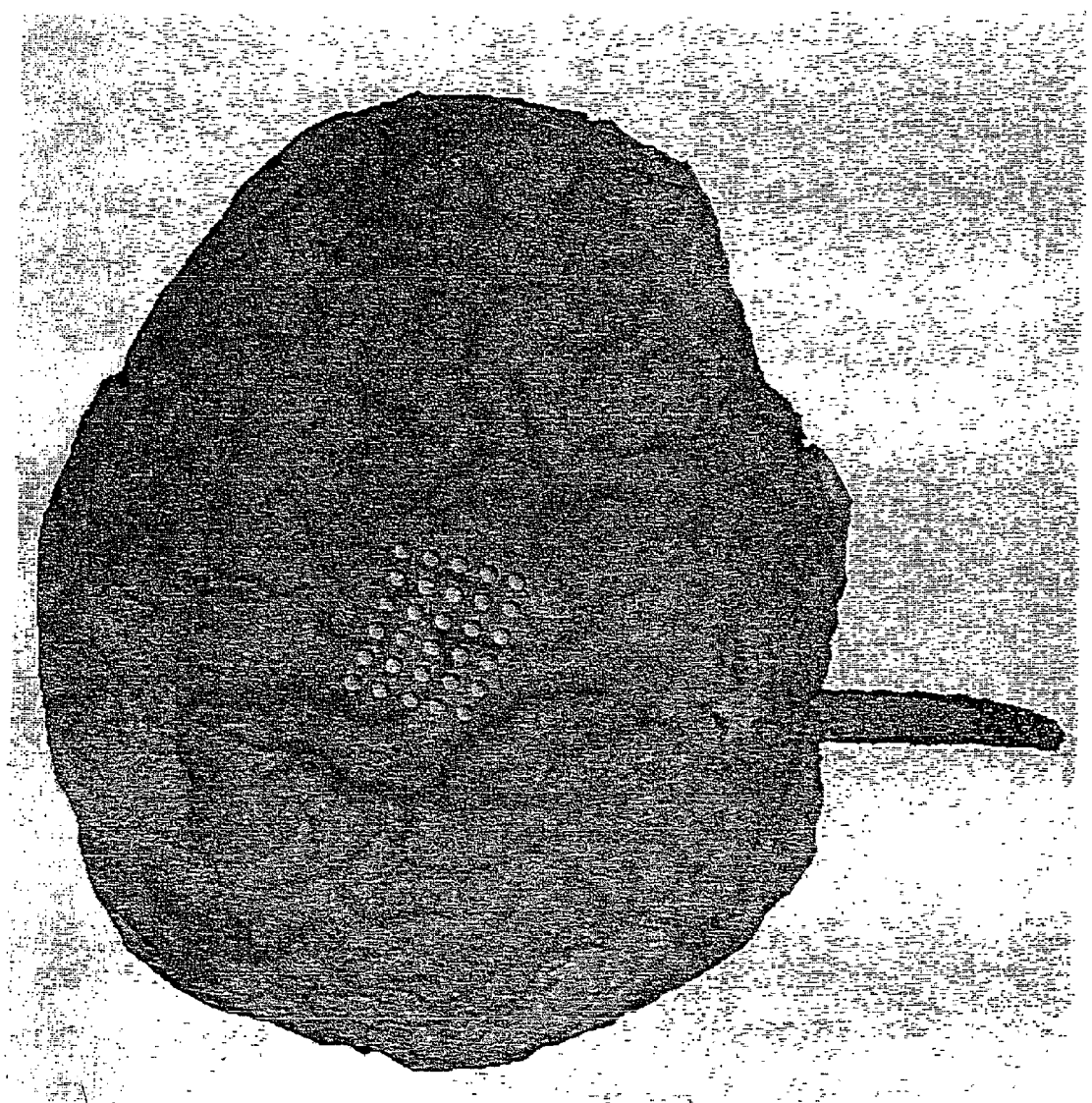
Figure 6A:
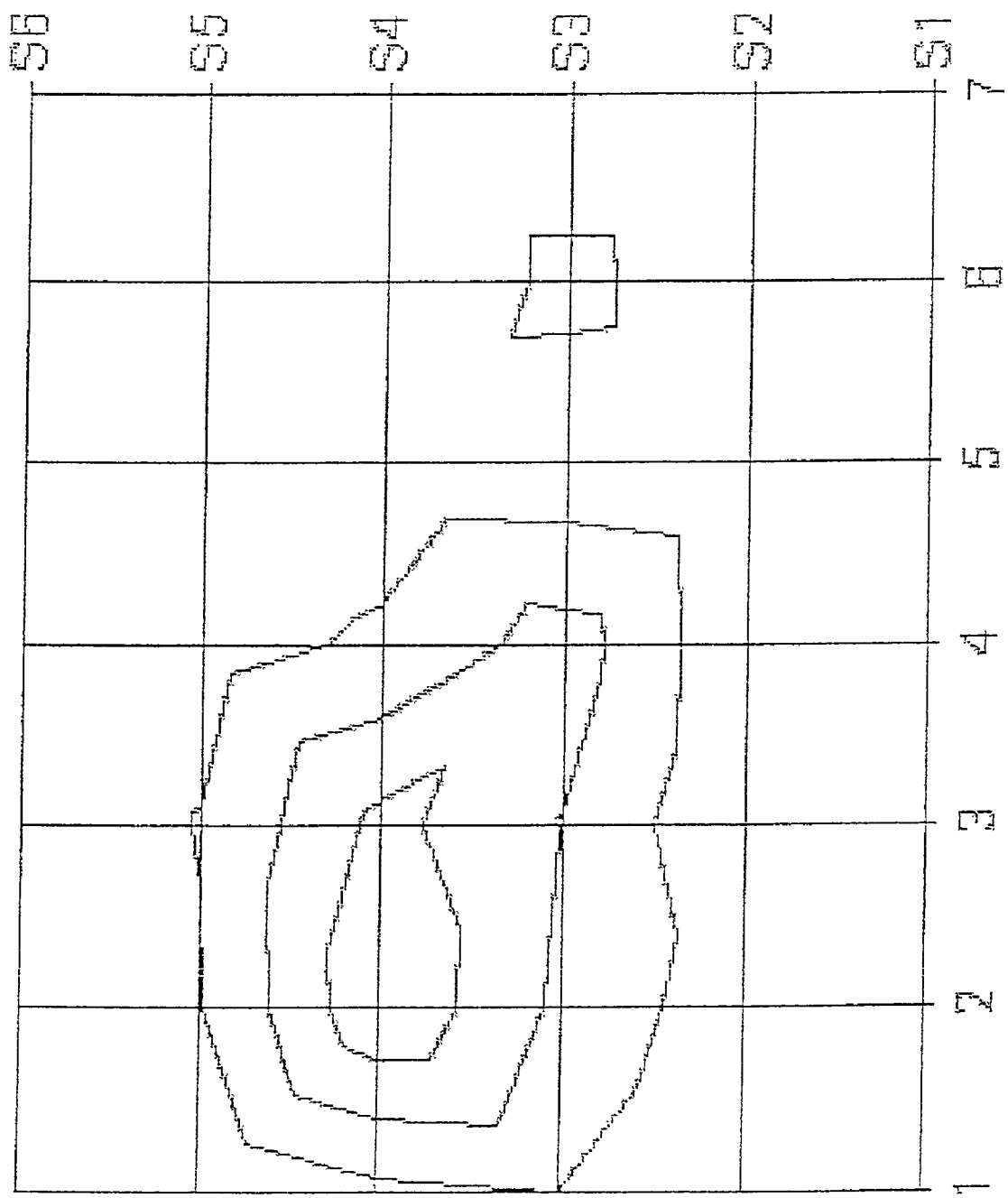
Figure 6B:
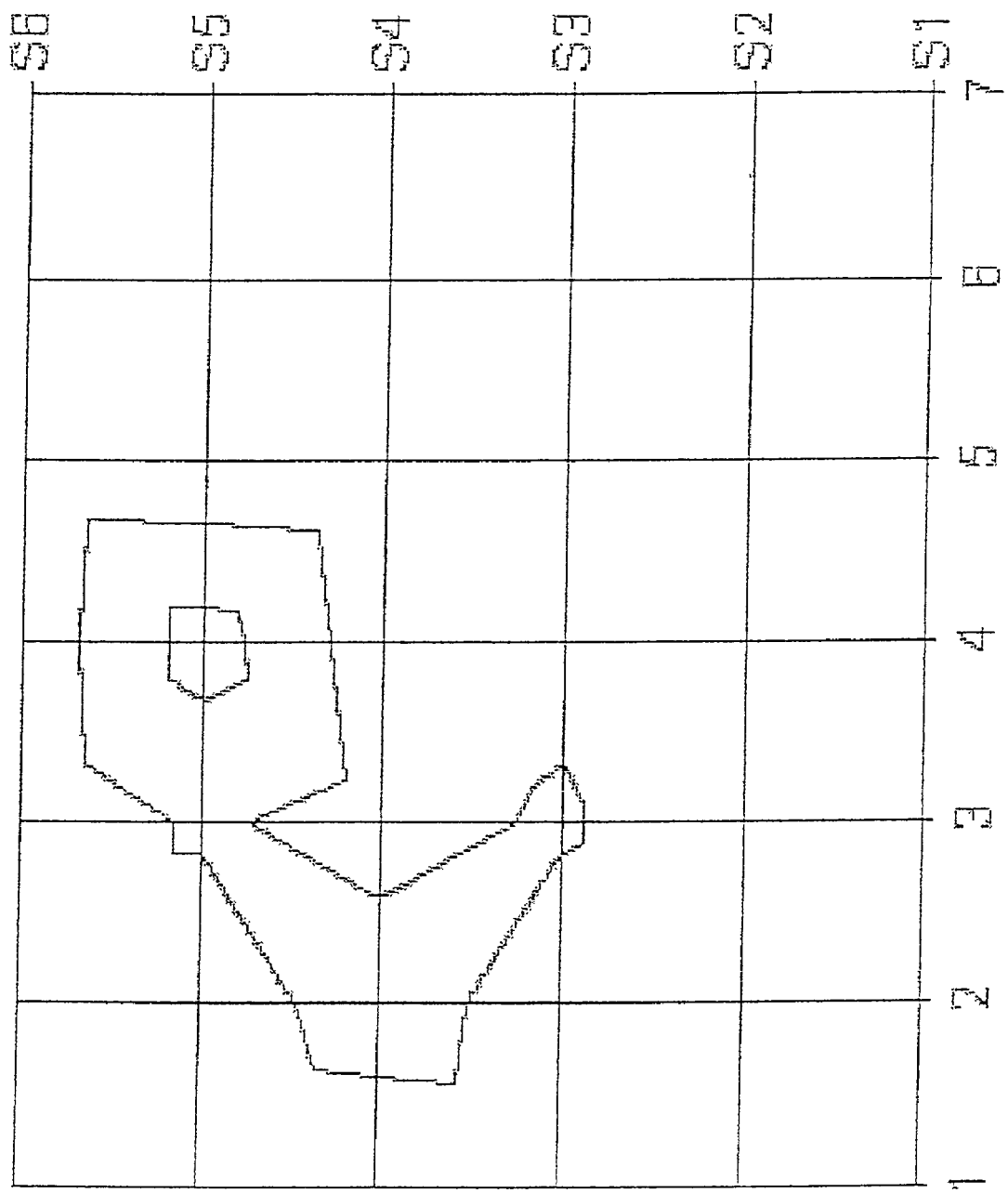
Figure 7C:
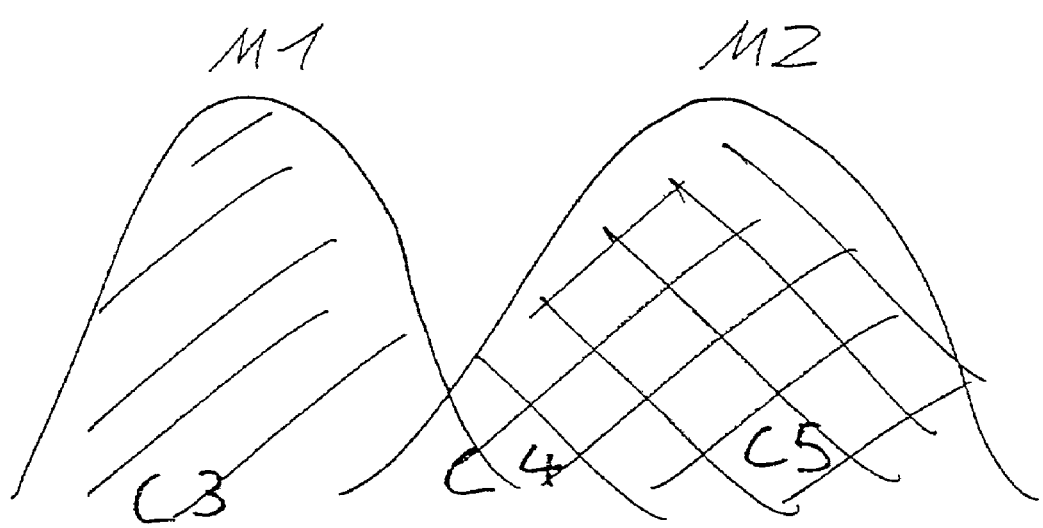
Figure 8A:
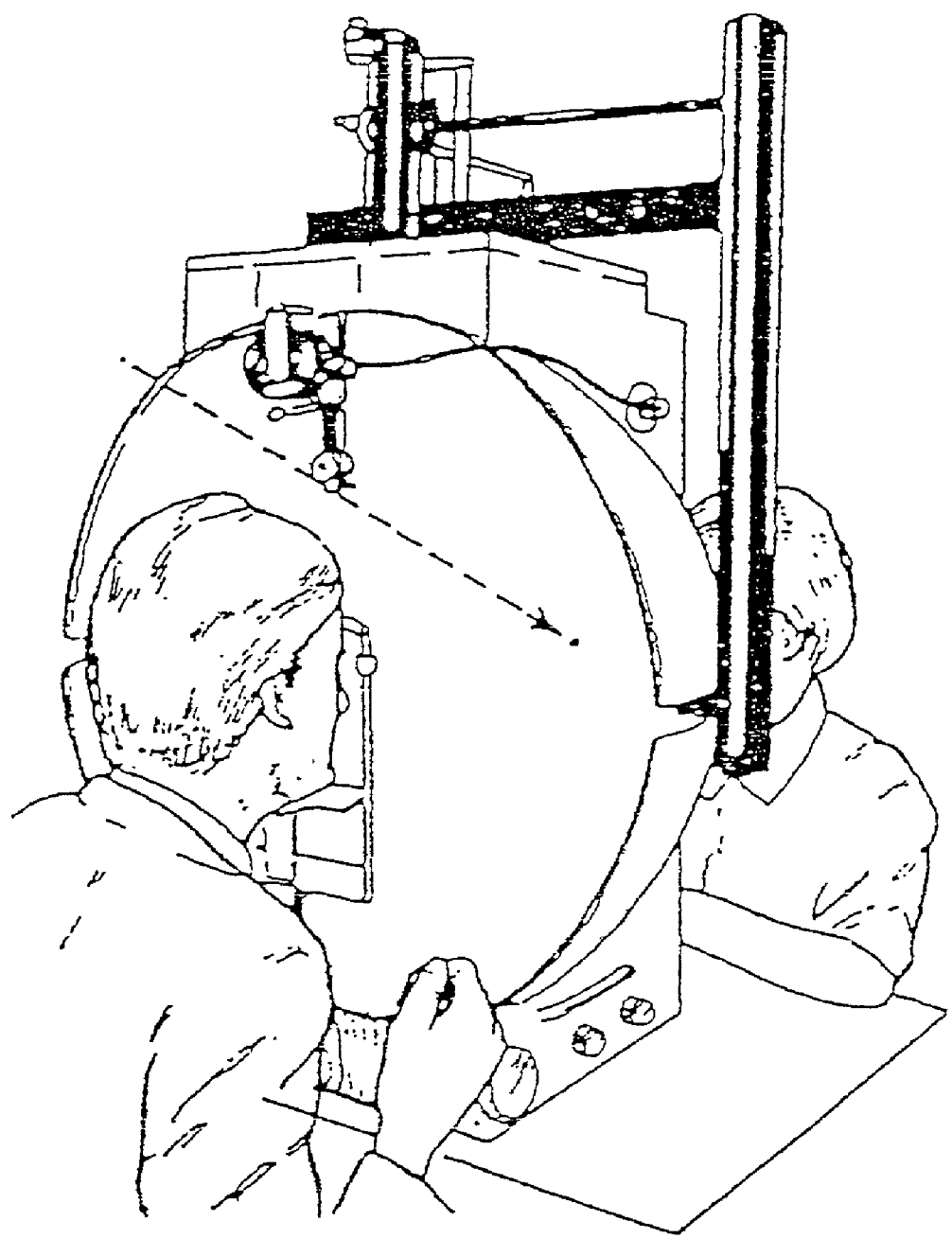
Figure 8B:
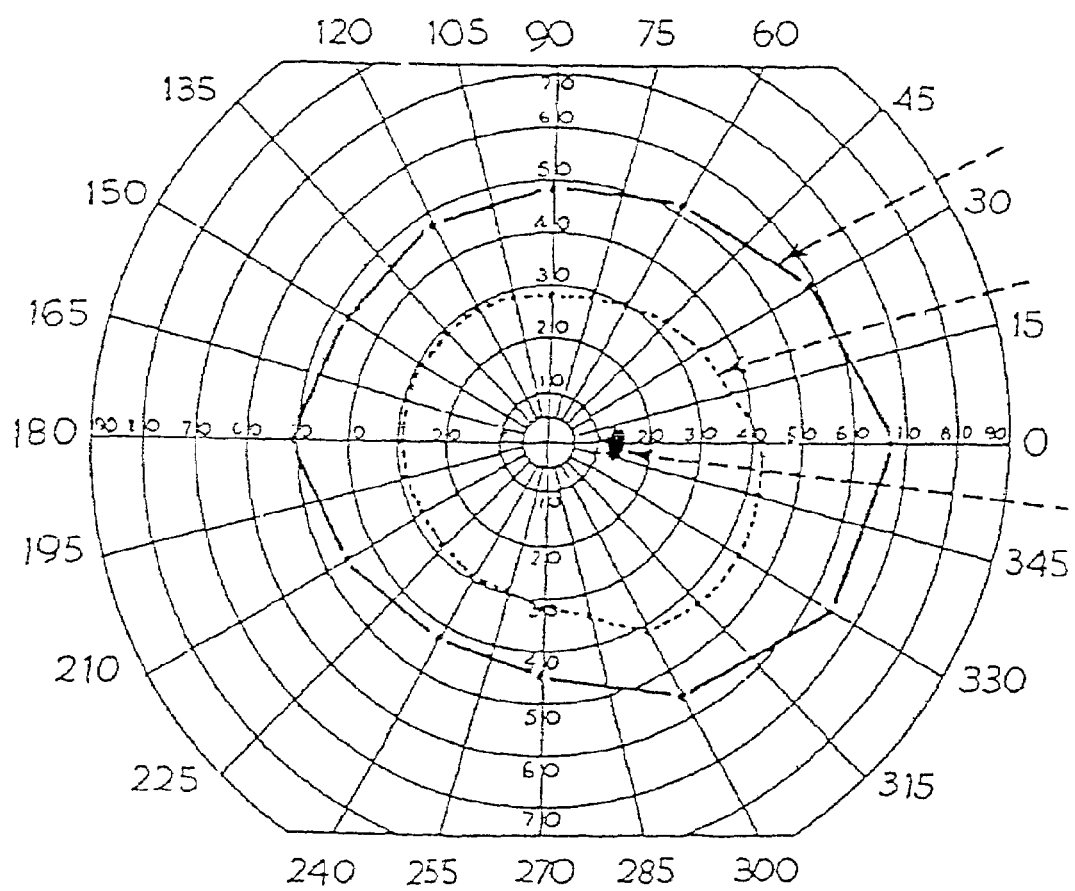
Figure 9:
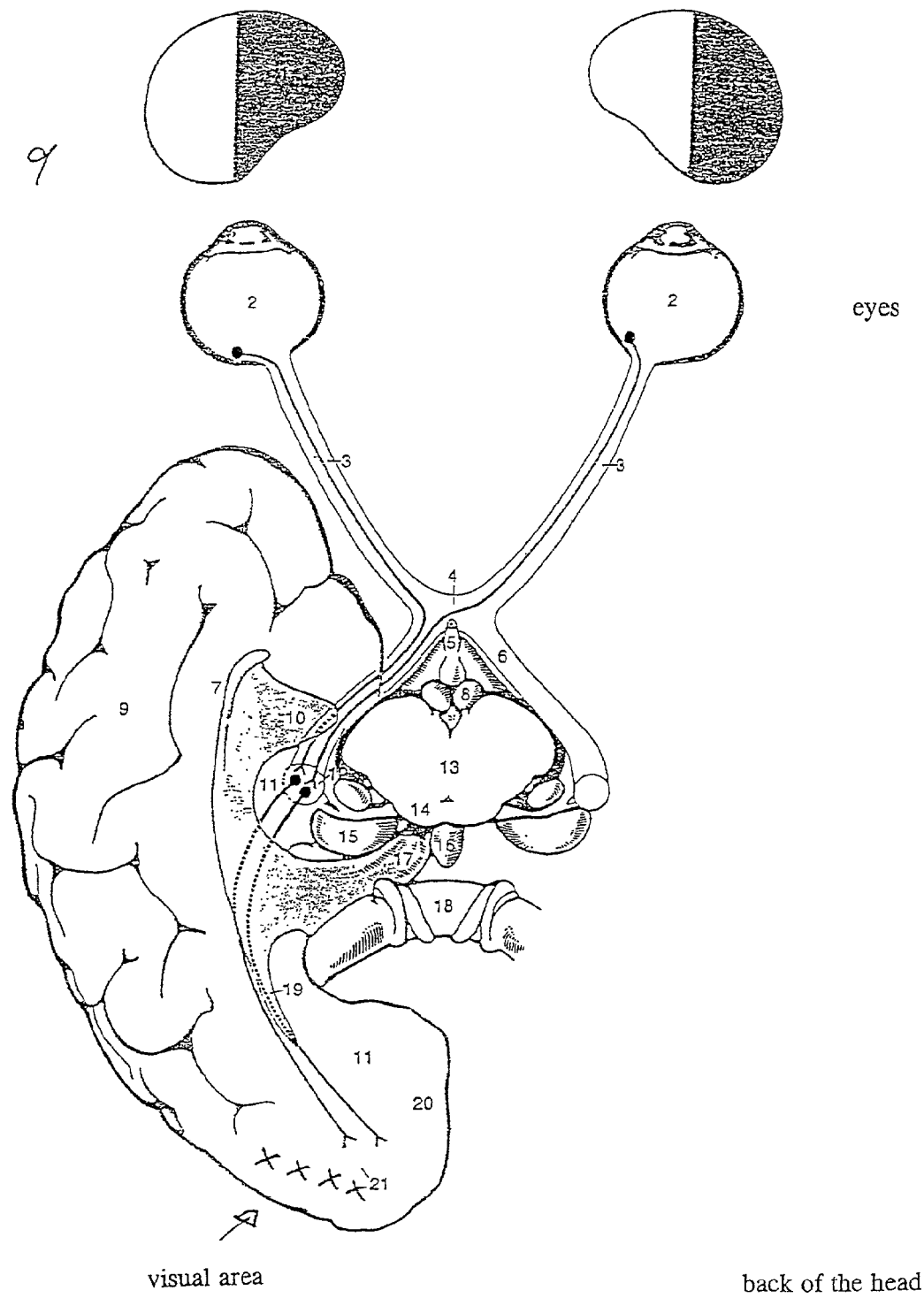
Figure 10:
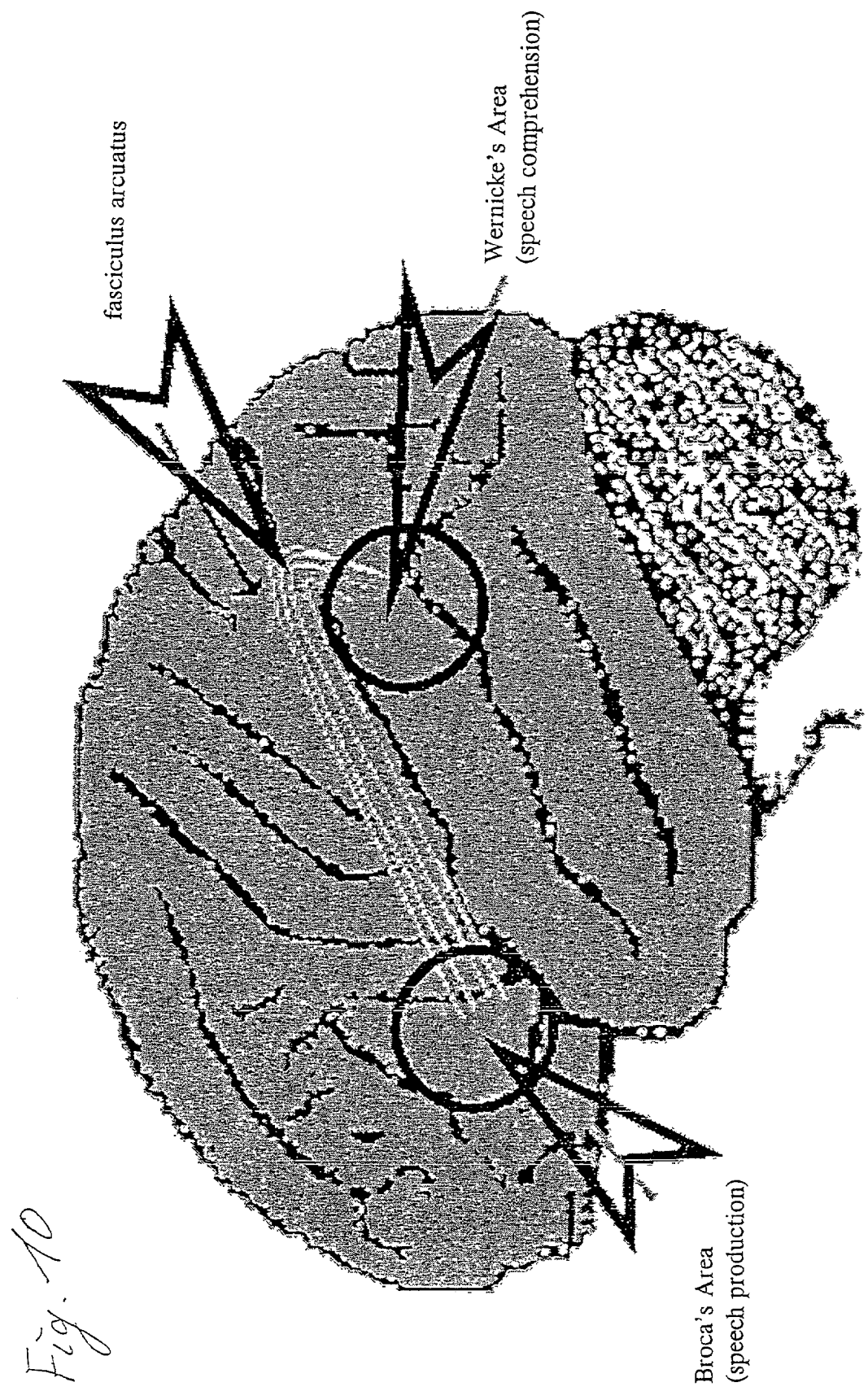

FIG. 4B the surface of a brain approximated in accordance with the invention, with a point of stimulation;

FIG. 5 shown schematically, a grid structure for generating stimulation patterns on the surface of the brain;

FIGS. 6A and 6B distribution functions on the surface of the brain for the grid for stimulus responses shown by way of example in FIG. 5, on two different muscles;

FIG. 7A a schematic representation of points of stimulation C3, C4 and C5 in a grid structure;

FIG. 7B the stimulus responses obtained for the two different muscles by stimulation at the points C3, C4 and C5; and FIG. 7C a schematic representation of a distribution function for the sensitivity of two muscles with respect to stimulation at the points C3, C4 and C5;

FIG. 8A an experimental arrangement for examining the visual cortex;

FIG. 8B a representation of the perimeter of the field of vision;

FIG. 9 a schematic representation of neuronal switching in the virtual system; and FIG. 10 a schematic representation of the areas of the brain important for speech.

FIG. 1 schematically shows the functions distributed over various areas of the brain, such as for example the visual, auditory, olfactory, motor, sensory and speech cortex. This rough division of the brain functions is substantially the same in all humans, and can be used as a first approximation for positioning a stimulation device in accordance with the invention and stimulating a particular area of the brain.

FIG. 2 shows, by way of example, the motor functions arranged on the gyrus precentralis, including how they are assigned to the respective muscles.

Examinations have already been performed many times, in order to be able to roughly map the brain functions, as shown in FIGS. 1 and 2. Such rough sub-dividing, however, can only be used as a starting point for another, more exact cortical cartography, which is performed in accordance with the invention as described above and which can be used for example to define as precisely as possible the function of a particular area of the brain.

FIG. 3A shows positions, indicated 1 to 9, for the left and right half of the brain, for positioning a stimulation device. If stimulation is performed using a method known in accordance with the prior art, then the actual distribution of the points of stimulation 1 to 9 for example, shown in FIG. 3B, occurs on the surface of the brain, which is a direct consequence of the inaccuracy of positioning the stimulation device hitherto, without position control, for example via the representation of the surface of the brain and the irregular structure of the surface of the brain, i.e. the surface of the brain does not run precisely parallel to the surface of the head.

In accordance with the invention, a data set obtained from a recording of a head or a brain using for example computer tomography or nuclear spin resonance, such as shown in FIG. 4A, is used to generate the three-dimensional model shown in FIG. 4B, consisting of a multitude of polygons, for approximating and three-dimensionally describing the surface of the brain. Based on the three-dimensional model of the surface of the brain shown in FIG. 4B, the suitable position of the stimulation device, such as for example a coil, can be calculated, for stimulating a particular area of the surface of the brain shown in FIG. 4B. To this end, the area of the surface of the brain to be stimulated is firstly determined. The surface element describing this area, or a mean value of a number of surface elements describing this area, is used to determine a line pointing outwards, normal on said area, as centrally as possible, wherein said line is intended for example to go through the center axis of an induction coil, in order to position the coil such that a current flowing through the coil generates the maximum magnetic field on the surface of the area thus determined, and a stimulation impulse is thus generated in the desired area of the surface of the brain, by induction. Due to the irregular structure of the surface of the brain, it can transpire that the best position for a coil is not normal on the surface of the head, but oblique to the normal, in order to stimulate a small area of the surface of the brain as precisely as possible.

FIG. 5 shows a field used in accordance with the invention for examining an area of the brain, stimulation impulses being generated sequentially and/or in parallel at the points shown.

FIGS. 6A and 6B show the intensities of stimulus responses for two different muscles, according to the location of the stimulation impulse or impulses. It can thus be seen from FIG. 6A, for example, that a first muscle shows the maximum response characteristic when it is stimulated at about the areas of the surface of the brain denoted by 2/S4 and 3/S4, while for the second muscle as shown in FIG. 6B, the maximum stimulus response when stimulated occurred at the point 4/S5. For examination, the individual points of stimulation can be stimulated both sequentially as well as in parallel, wherein a number of muscles are simultaneously monitored in accordance with the invention, in order to be able to deduce the distribution of the brain functions and/or the assignment of individual motor functions to individual areas of the brain, from the multi-channel recording thus obtained.

FIG. 7A schematically shows a grid structure, wherein stimulation signals are applied to the surface of the brain at the points C3, C4 and C5. For predetermined stimulation signals, stimulus responses of different strengths result at these points for the two different muscles, as shown in FIG. 7B. Based on these stimulus responses of different strengths, a distribution function or sensitivity function of the surface of the brain with respect to these muscles can be produced, as shown schematically in FIG. 7C. In other words, the muscle M1 can best be stimulated at about the point C3, while the muscle M2 can best be stimulated at the point C5.

FIG. 8A shows an experimental arrangement for examining the visual cortex, wherein a test person is supposed to fix a particular point. As shown in FIG. 8B in the example of the right eye, there is a blind spot—at which no optical stimuli can be perceived—in the field of vision, on the right next to the fixing point. The central field of vision is marked in broken lines and the peripheral field of vision in continuous lines. A test person receiving TMS stimulation signals by induction is to state in which area of the field of vision the stimulation signal generates a flash, or which area of the field of vision can no longer be perceived due to an inhibiting signal, so as to be able to map the visual cortex, i.e. to be able to assign the fields of vision of the left and right eye to individual structures on the visual cortex.

FIG. 9 schematically shows the neuronal switching in the visual system, in a view from below. Here, the visual area is marked, in which the TMS examinations mentioned above are performed.

FIG. 10 schematically shows the areas of the brain important for speech.

Broca's Area serves to generate speech, Wernicke's Area serves to interpret what has been spoken. These areas are inter-linked. As opposed to the other functional areas, speech is generally localized on one half of the brain only, however there is very high individual variance in this respect.

The invention claimed is:

1. A method for stimulating and/or inhibiting at least one point or area of a brain using at least one stimulation device, comprising:
   a) recording a spatial structure of the head or brain;
   b) generating a three-dimensional simulation model of the surface of the brain from the recording of the spatial structure of the brain; and
   c) arranging the stimulation device relative to the head or brain using the three-dimensional simulation model of the surface of the brain, whereby the stimulation device is accurately positioned relative to the surface of the brain, wherein the stimulation device is positioned such that a magnetic field generated or generable by the stimulation device is normal to the simulation model of the surface of the brain on or over the area to be stimulated or exhibits a predetermined spatial angle relative to the simulation model of the surface of the brain.

2. The method as set forth in claim 1, wherein the spatial structure of the head or brain is recorded using a nuclear spin resonance, computer tomography, x-ray or ultrasound method.

3. The method as set forth in claim 1, wherein the simulation model of the surface of the brain is formed by a plurality of polygons.

4. The method as set forth in claim 1, wherein one or more coils are used as the stimulation device.

5. The method as set forth in claim 1, wherein the stimulation device is navigated to a calculated position for the desired stimulation.

6. The method as set forth in claim 1, wherein a stimulation signal is only released or generated when the deviation of a calculated position of the stimulation device from the actual position of the stimulation device is smaller than a predetermined value or keeps within a predetermined angular range.

7. The method as set forth in claim 1, wherein positional data for the stimulation device and/or the brain or head and/or the electrical field which may be induced on the surface of the brain are displayed.

8. The method as set forth in claim 1, wherein a simulation model of the stimulation device and/or the head and/or the brain is used.

9. The method as set forth in claim 8, wherein the simulation model is a multi-shell model.

10. A computer program embodied on a computer readable medium for stimulating and/or inhibiting at least one point or area of a brain using at least one stimulation device, comprising:
a) code that records a spatial structure of the head or brain;
b) code that generates a three-dimensional simulation model of the surface of the brain from the recording of the spatial structure of the brain; and
c) code that arranges the stimulation device relative to the head or brain using the three-dimensional simulation model of the surface of the brain, whereby the stimulation device is accurately positioned relative to the surface of the brain, wherein the stimulation device is positioned such that a magnetic field generated or generable by the stimulation device is normal to the simulation model of the surface of the brain on or over the area to be stimulated or exhibits a predetermined spatial angle relative to the simulation model of the surface of the brain.

11. A device for stimulating and/or inhibiting at least one point or area of a brain, comprising:
a recording device for detecting the spatial structure of the brain;
a computational device for generating a simulation model of the surface of the brain and at least one stimulation or induction device; and
a navigation device for positioning the stimulation or induction device, wherein the navigation device is configured to use the simulation model of the surface of the brain to arrange the stimulation device relative to the brain such that a magnetic field generated or generable by the stimulation device is normal or arranged at a predetermined angle with respect to the simulation model of the surface of the brain on or over the area to be stimulated.

12. The device as set forth in claim 11, wherein markers are provided on the head and/or on the brain and/or on the stimulation device, for navigating and positioning the stimulation device relative to the brain.

13. The device as set forth in claim 11, comprising a control system with which the stimulation device can be positioned by a method wherein the spatial structure of the head or brain is recorded; a three-dimensional simulation model of the surface of the brain is generated from the recording of the spatial structure of the brain; and the stimulation device is arranged relative to the head or brain using the three-dimensional simulation model of the surface of the brain, such that the at least one point or area of a brain can be stimulated using the stimulation device.

14. The device as set forth in claim 11, wherein a display device is provided for displaying the position of the head or brain relative to the stimulation device and/or for displaying the stimulation signal generated or generable by the stimulation device, in particular an induced electrical field or signal.

15. A method for determining the function of a particular area of the brain, comprising:
stimulating at least one particular area using a stimulation device; and
measuring the stimulus response at least two different positions, wherein the stimulation device is arranged relative to the brain using a three-dimensional simulation model of the surface of the brain such that a magnetic field generated or generable by the stimulation device is normal or arranged at a predetermined angle with respect to the simulation model of the surface of the brain on or over the area to be stimulated.

16. The method as set forth in claim 15, wherein at least two positions on a grid structure are provided for stimulating various areas of the brain sequentially or in parallel.

17. The method as set forth in claim 15, wherein at least two stimulus detection devices detect a strength of the stimulus response.

18. The method as set forth in claim 15, wherein stimulation signals are applied in an area of the motor cortex.

19. The method as set forth in claim 15, wherein a computer-guided or navigated stimulation device is used to generate stimulation signals.

20. The method as set forth in claim 15, wherein at least one stimulation device is positioned by a method wherein the spatial structure of the head or brain is recorded; a three-dimensional simulation model of the surface of the brain is generated from the recording of the spatial structure of the brain; and the stimulation device is arranged relative to the head or brain using the three-dimensional simulation model of the surface of the brain, such that the at least one point or area of a brain can be stimulated using the stimulation device.

21. The method as set forth in claim 15, wherein a mean value is formed from a number of stimulus responses for substantially the same stimulation signals.

22. The method as set forth in claim 15, wherein a stimulus sensitivity function is generated for at least one muscle, in accordance with the position on the surface of the brain.

23. A computer program embodied on a computer readable medium for determining the function of a particular area of the brain, wherein at least one particular area is stimulated using a stimulation device and the stimulus response is measured at least two different positions, comprising code that directs the arrangement of the stimulation device relative to the brain using a three-dimensional simulation model of the surface of the brain such that a magnetic field generated or generable by the stimulation device is normal or arranged at a predetermined angle with respect to the simulation model of the surface of the brain on or over the area to be stimulated.

24. A device for determining the function of a particular area of the brain, comprising:
at least one stimulation device;
at least two stimulus detection devices; and
a navigation device for positioning the stimulation device, wherein the navigation device is configured to use a simulation model of the surface of the brain to arrange the stimulation device relative to the brain such that a magnetic field generated or generable by the stimulation device is normal or arranged at a predetermined angle with respect to the simulation model of the surface of the brain on or over the area to be stimulated.

25. The device as set forth in claim 24, wherein at least two stimulation devices are provided, arranged in a grid structure.

26. The device as set forth in claim 24, further comprising a control device configured to record a spatial structure of the head or brain, and to generate a three-dimensional simulation model of the surface of the brain from the recording of the spatial structure of the brain, wherein the stimulation device is arranged relative to the head or brain using the three-dimensional simulation model of the surface of the brain, such that the at least one point or area of a brain can be stimulated using the stimulation device.

* * * * *